(12) United States Patent
Kawarada

(10) Patent No.: US 6,833,059 B2
(45) Date of Patent: Dec. 21, 2004

(54) FIELD-EFFECT TRANSISTOR

(75) Inventor: Hiroshi Kawarada, Yokohama (JP)

(73) Assignee: Japan Science and Technology Corporation (JP)

( * ) Notice: Subject to any disclaimer, the term of this patent is extended or adjusted under 35 U.S.C. 154(b) by 232 days.

(21) Appl. No.: 09/959,905

(22) PCT Filed: Mar. 26, 2001

(86) PCT No.: PCT/JP01/02394
§ 371 (c)(1),
(2), (4) Date: Nov. 13, 2001

(87) PCT Pub. No.: WO01/73421
PCT Pub. Date: Oct. 4, 2001

(65) Prior Publication Data
US 2002/0157949 A1 Oct. 31, 2002

(30) Foreign Application Priority Data
Mar. 27, 2000  (JP) ........................................ 2000-085947

(51) Int. Cl.[7] .................... G01N 27/327; G01N 27/414; H01L 23/58
(52) U.S. Cl. .................. 204/403.01; 257/253
(58) Field of Search ................ 204/416–419, 204/403.13, 403.01; 257/213, 77, 249, 235, 236, 252, 253

(56) References Cited

U.S. PATENT DOCUMENTS 5,362,975 A * 11/1994 von Windheim et al. ..... 257/76
5,776,323 A * 7/1998 Kobashi ..................... 204/294

FOREIGN PATENT DOCUMENTS

| GB | 2328023 A | * 2/1999 | ............ C12Q/1/00 |
| JP | 61-33645 | 2/1986 | ............ A61B/5/14 |
| JP | 4-258754 | 9/1992 | ......... G01N/27/414 |
| JP | 8-240555 | 9/1996 | ......... G01N/27/327 |

OTHER PUBLICATIONS

Voigt et al. ("Diamond–like carbon–gate pH–ISFET," Sensors and Actuators B 44 (1997) 441–445).*

* cited by examiner

Primary Examiner—Alex Noguerola
(74) Attorney, Agent, or Firm—Lorusso, Loud & Kelly

(57) ABSTRACT

An object is to provide a field effect transistor which uses a liquid electrolyte as a gate and which operates stably in the liquid electrolyte.

A field effect transistor includes a channel (2) formed of a portion of a hydrogen-terminated surface of a diamond, the portion being exposed to the outside between a gate electrode (3) and a drain electrode (6); and a gate formed of a liquid electrolyte (4) in contact with the exposed portion of the hydrogen-terminated surface of the diamond.

11 Claims, 9 Drawing Sheets

F I G. 1
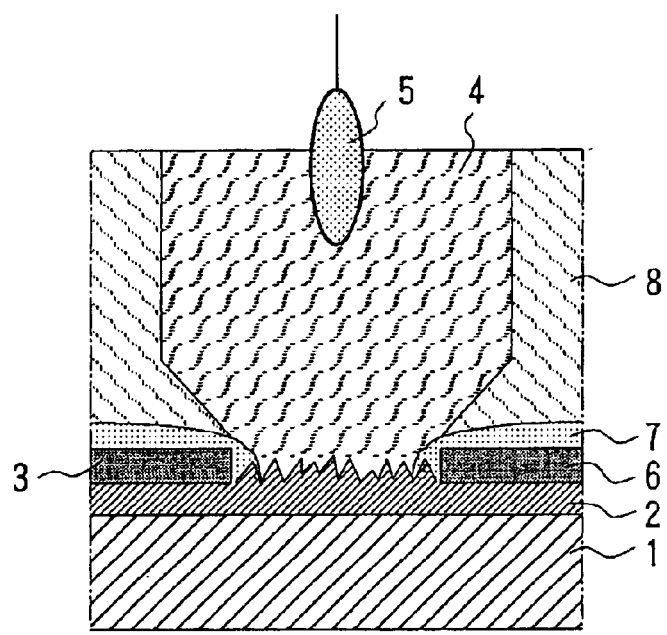
F I G. 2
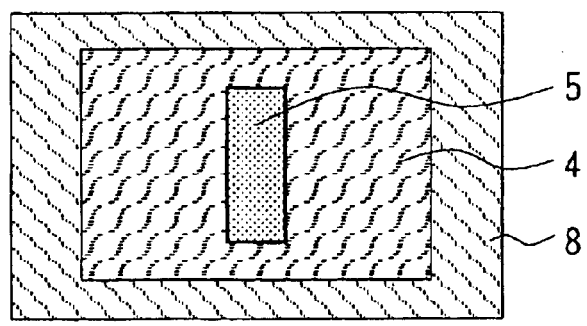

FIELD-EFFECT TRANSISTOR

TECHNICAL FIELD

The present invention relates to a field effect transistor which uses liquid electrolyte as a gate and a hydrogen-terminated surface of diamond as a channel.

BACKGROUND ART

An undoped hydrogen-terminated diamond thin film formed by a microwave plasma CVD method has been known to have a p-type conductive layer formed on its surface, regardless of whether the diamond thin film is monocrystalline or polycrystalline. Thus far, the present inventors have fabricated a field effect transistor (FET) in which deposition of metal or insulating substance on the gate portion is avoided through utilization of such a surface conductive layer and have tested the operation of the FET within an electrolytic aqueous solution (Ken-ichi Kitatani, et al., Proceedings of the 46th Applied Physics Joint Lecture Meeting, 30a-P7-22 (1999) pp. 628).

Further, an electric double layer is considered to be formed at the interface between a surface conductive layer of a diamond in an electrolytic solution and the electrolyte (Takeshi Hosomi, et al., Abstracts of the 13th Diamond Symposium Lecture Meeting, 115 (1999) pp. 36).

DISCLOSURE OF THE INVENTION

The present inventors have tackled development of an ISFET biosensor in which an ion sensitive field effect transistor (ISFET) is used as a transducer, and an enzyme is used as a molecular recognizing substance, and have found that such an ISFET biosensor can be used as a micro-sensor for clinical test, industrial measurement, and environmental measurement, with possible future application to a body-embedable sensor.

However, at present, such an ISFET biosensor has a practical problem in that even when the molecular recognizing substance functions properly and an intended molecule is selected, operation of the ISFET itself becomes unstable due to a substance invading from outside the sensor. This unstable condition is caused by a great variation in threshold voltage attributable to generation of an interface level, or presence of ions at the oxide film/Si interface, which is the most delicate portion within an Si MOSFET. When a sensor is used, its surface is unavoidably exposed to the atmosphere. In the case of an ion sensor or biosensor, even when a protective layer is used, a considerably large number of undesired molecules or ions invade the oxide film/Si interface as compared with the case of LSIs. Therefore, creation of a chemically strong semiconductor surface is indispensable for development of ISFET biosensors.

Incidentally, a hydrogen-adsorbed surface (hydrogen-terminated surface) of diamond is stable up to 700° C. in vacuum, and up to 300° C. in the atmosphere; is chemically inert even in liquid; and, near room temperature, does not cause structure change even when exposed to strong acid or strong alkali. In addition, a p-type conductive layer is formed in the vicinity of the hydrogen-terminated diamond surface.

On the basis of the above-described research, the present inventors have developed an FET in which a liquid electrolyte is used as a gate.

In view of the foregoing, an object of the present invention is to provide a field effect transistor which uses a liquid electrolyte as a gate and which operates stably in the liquid electrolyte.

In order to achieve the above object, the present invention provides the following.

[1] A field effect transistor characterized by comprising a channel formed of a portion of a hydrogen-terminated surface of a diamond, the portion being exposed to the outside between a source electrode and a drain electrode; and a gate formed of a liquid electrolyte in contact with the exposed portion of the hydrogen-terminated surface of the diamond.

[2] A field effect transistor as described in [1] above, characterized in that the diamond is formed of an undoped, hydrogen-terminated, monocrystalline or polycrystalline diamond thin film.

[3] A field effect transistor as described in [1] above, characterized in that the channel is a p channel.

[4] A field effect transistor as described in [1] above, characterized in that the p channel can be pinched off.

[5] A field effect transistor as described in [1] above, characterized in that the p channel is of a normally off type.

[6] A field effect transistor as described in [1] above, characterized in that the hydrogen-terminated surface of the diamond has a wide potential window, and the field effect transistor operates accurately within the range of the potential window.

[7] A field effect transistor as described in [1] above, characterized in that the liquid electrolyte is an alkaline solution.

[8] A field effect transistor as described in [7] above, characterized in that the liquid electrolyte is a KOH aqueous solution.

[9] A field effect transistor as described in [1] above, characterized in that the liquid electrolyte is an acidic solution.

[10] A field effect transistor as described in [1] above, characterized by having a threshold voltage which exhibits low dependence on the pH of the liquid electrolyte.

[11] A field effect transistor as described in [1] above, characterized by having a threshold voltage which is not affected by the environment.

BRIEF DESCRIPTION OF THE DRAWINGS

FIG. 1 is a cross-sectional view of a liquid-electrolyte-gate diamond FET (p-channel FET) according to the present invention;

FIG. 2 is a plan view of the liquid-electrolyte-gate diamond FET (p-channel FET) according to the present invention;

BEST MODE FOR CARRYING OUT THE INVENTION

Figure 3:
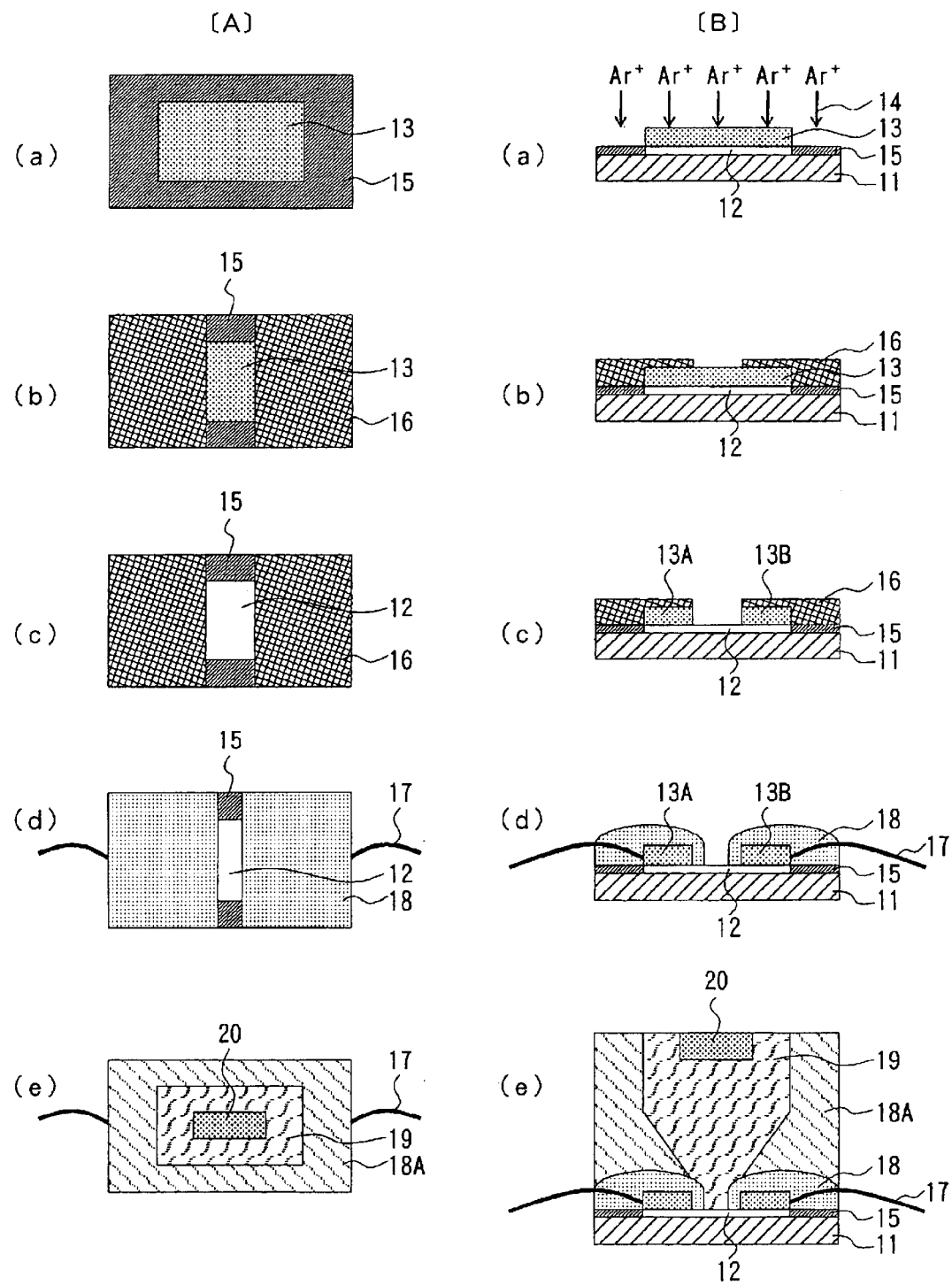
FIG. 3 shows steps of a method for fabricating a liquid-electrolyte-gate diamond FET according to a first embodiment of the present invention.

Embodiments of the present invention will next be described in detail.

FIG. 1 is a cross-sectional view of a liquid-electrolyte-gate diamond FET (p-channel FET) according to the present invention, and FIG. 2 is a plan view of the FET.

In these drawings, reference numeral 1 denotes a polycrystalline diamond serving as a substrate; 2 denotes a channel (terminated surface of the polycrystalline diamond: p-type surface conductive layer); 3 denotes a source electrode (Au electrode); 4 denotes a gate (liquid electrolyte: e.g., KOH aqueous solution); 5 denotes a gate electrode; 6 denotes a drain electrode (Au electrode); 7 denotes a protective film; and 8 denotes a liquid vessel (insulator).

Drain current is controlled by gate voltage and can be pinched off completely. The threshold voltage of the FET varies within the range of ±0.2 V when pH of the liquid electrolyte varies from 1 to 14, does not show Nernst response, and exhibits almost no pH dependency. The operation voltage range of the FET corresponds to the range of an electric potential window in the case where diamond is used as an electrochemical electrode. The diamond is monocrystalline or polycrystalline, and the surface of the diamond is covered with hydrogen atoms.

A method of fabricating the above-described liquid-electrolyte-gate diamond FET will be described.

FIG. 3 shows steps of a method for fabricating the liquid-electrolyte-gate diamond FET according to a first embodiment of the present invention, wherein FIG. 3[A] shows top views of the diamond FET in the respective steps; and FIG. 3[B] shows cross-sectional views of the diamond FET in the respective steps.

Metal is vapor-deposited all over the surface to form a metal film, and a portion of the metal film corresponding to a gate portion is removed by means of photolithography. Gold, which forms ohmic contact with a diamond thin film, is used as the metal. The metal film forms pads, a source electrode, and a drain electrode. In this connection, the gate length is set to 1 mm.

The fabrication method according to the first embodiment will be described in detail with reference to FIG. 3.

(1) An Au layer 13 is vapor-deposited on the entire surface of a sample (terminated surface of a polycrystalline diamond) 11, and then photoresist AZ is applied to the entire surface. Application conditions are such that a spinner is rotated at 1,500 rpm for 5 sec and then at 5,000 rpm for 15 sec. Subsequently, the sample is masked such that the Au layer 13 remains at the central portion of the sample, and is then exposed to light, followed by development. Then, a p-type surface conductive layer 12 is formed on the surface of the sample 11. A portion of the Au layer 13 which is not protected by the resist is removed through etching performed by use of potassium iodide. Subsequently, the resist is removed, and Ar ions 14 are implanted into the exposed hydrogen-terminated surface of the diamond by use of a medium current ion implanter in order to destroy the p-type surface conductive layer 12 to thereby form an element separation region 15. The element separation 15 prevents leakage of current from the periphery. The dose is $2\times10^{13}/cm^2$ (see (a) of FIG. 3[A] and (a) of FIG. 3[B]).

(2) Photoresist is again applied to the entire surface; and the sample is covered with a mask 16 such that a portion of the Au layer 13 corresponding to the gate is exposed. Subsequently, the sample is exposed to light and developed (see (b) of FIG. 3[A] and (b) of FIG. 3[B]).

(3) Subsequently, after removal of the exposed portion of the Au layer 13 through etching performed by use of potassium iodide (see (c) of FIG. 3[A] and (c) of FIG. 3[B]), the mask 16 is removed. Thus, a source electrode 13A and a drain electrode 13B are formed.

(4) Subsequently, the substrate is bonded to a slide; and lead wires 17 are connected to the electrodes. Subsequently, epoxy resin (protective layer) 18 is applied to the substrate for waterproofing (see (d) of FIG. 3[A] and (d) of FIG. 3[B]).

(5) Finally, a liquid electrolyte 19 of an alkali aqueous solution is charged into the exposed gate portion; and a gate electrode 20 is formed. Reference numeral 18A denotes a liquid vessel made of an insulating material.

Figure 4:
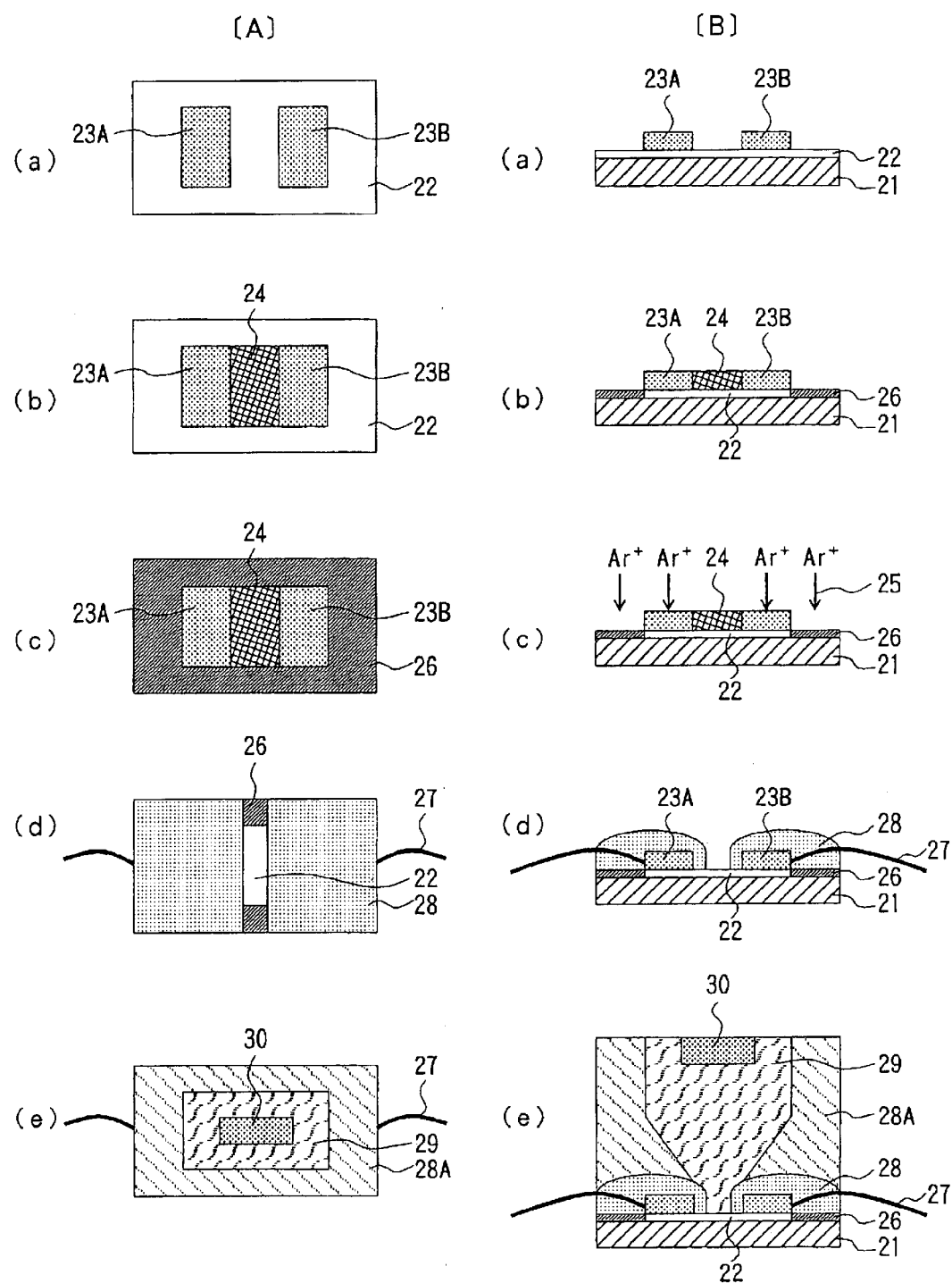
FIG. 4 shows steps of a method for fabricating a liquid-electrolyte-gate diamond FET according to a second embodiment of the present invention.

FIG. 4 shows steps of a method for fabricating a liquid-electrolyte-gate diamond FET according to a second embodiment of the present invention, wherein FIG. 4[A] shows top views of the diamond FET in the respective steps; and FIG. 4[B] shows cross-sectional views of the diamond FET in the respective steps.

The above described fabrication method according to the first embodiment involves troublesome work of applying resist twice, resulting in a long fabrication time. In order to simplify the process, in the fabrication method according to the second embodiment, a metal mask is fabricated in order to eliminate necessity of etching of the gate portion. A molybdenum plate is used for the metal mask such that only source and drain portions are formed from the beginning. In addition, the gate length is reduced from 1 mm to 0.5 mm.

The fabrication method according to the second embodiment will be described in detail with reference to FIG. 4.

(1) First, through use of a metal mask (not shown), Au is vapor-deposited on a sample (terminated surface of the polycrystalline diamond) 21 to thereby form a source electrode 23A and a drain electrode 23B (see (a) of FIG. 4[A] and (a) FIG. 4[B]). Reference numeral 22 denotes a p-type surface conductive layer.

(2) Subsequently, resist 24 (OEBR2000) is applied to the gate portion (see (b) of FIG. 4[A] and (b) FIG. 4[B]).

(3) Subsequently, by use of a medium current ion implanter, the p-type surface conductive layer 22 other than portions corresponding to the gate portion and the electrodes is destroyed by means of Ar ions 25, so that an element separation region 26 is formed. The dose is $2\times10^{13}/cm^2$ (see (c) of FIG. 4[A] and (c) FIG. 4[B]).

(4) After removal of the resist 24, the substrate is bonded to a slide; and lead wires 27 are connected to the electrodes. Subsequently, epoxy resin (a protective layer) 28 is applied to the substrate for waterproofing (see (d) of FIG. 4[A] and (d) of FIG. 4[B]).

(5) Finally, a liquid electrolyte 29 of an alkali aqueous solution is charged into the exposed gate portion; and a gate electrode 30 is formed (see (e) of FIG. 4[A] and (e) of FIG. 4[B]). Reference numeral 28A denotes a liquid vessel made of an insulating material.

The fabrication method of the present embodiment greatly simplifies the fabrication steps as compared with the case of the first fabrication method, so that the time required for fabricating an FET can be reduced to half.

Figure 5:
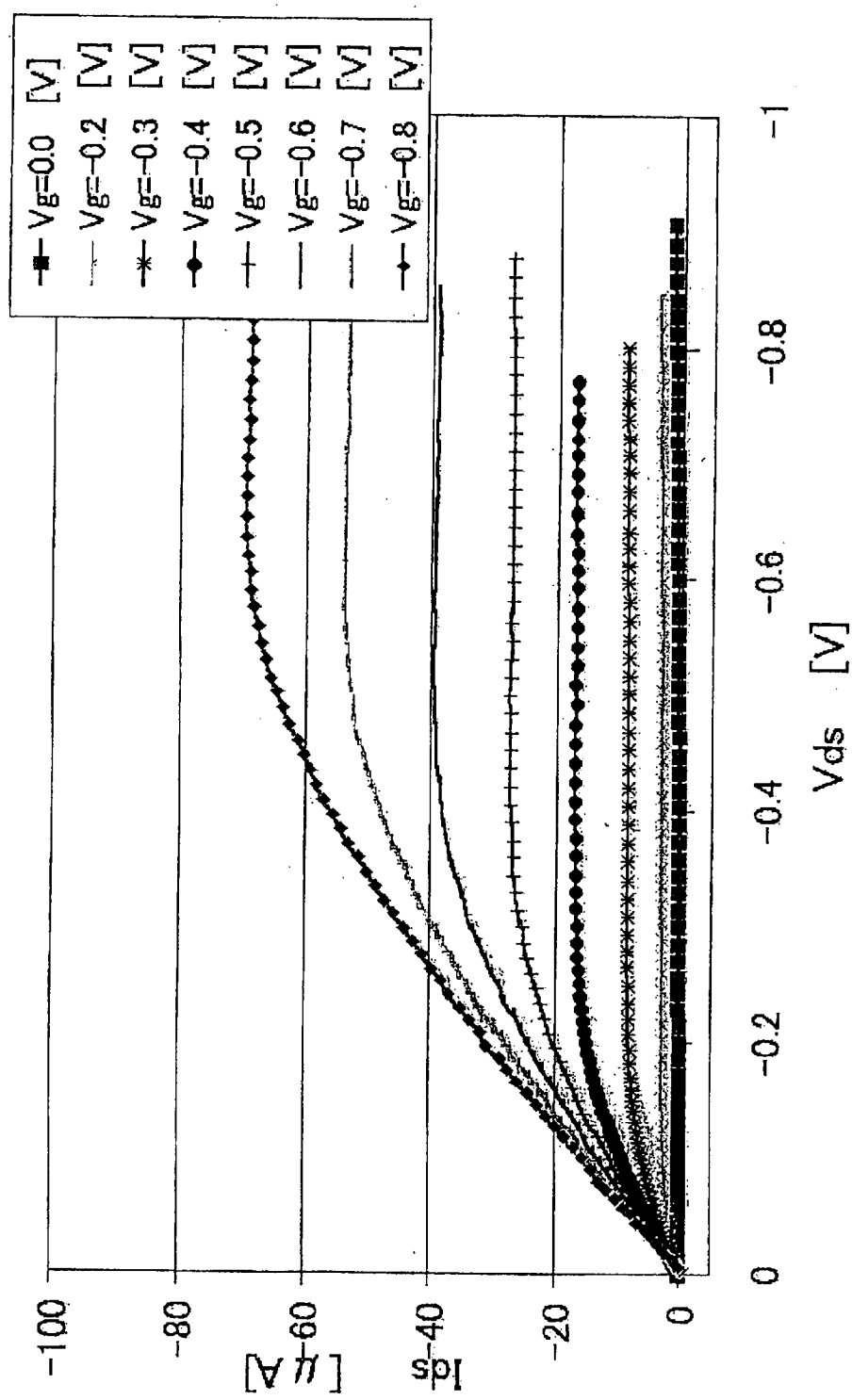
FIG. 5 is a graph showing static characteristics of the liquid-electrolyte-gate diamond FET fabricated by the second embodiment of the present invention (KOH aqueous solution; pH: 11)
Figure 6:
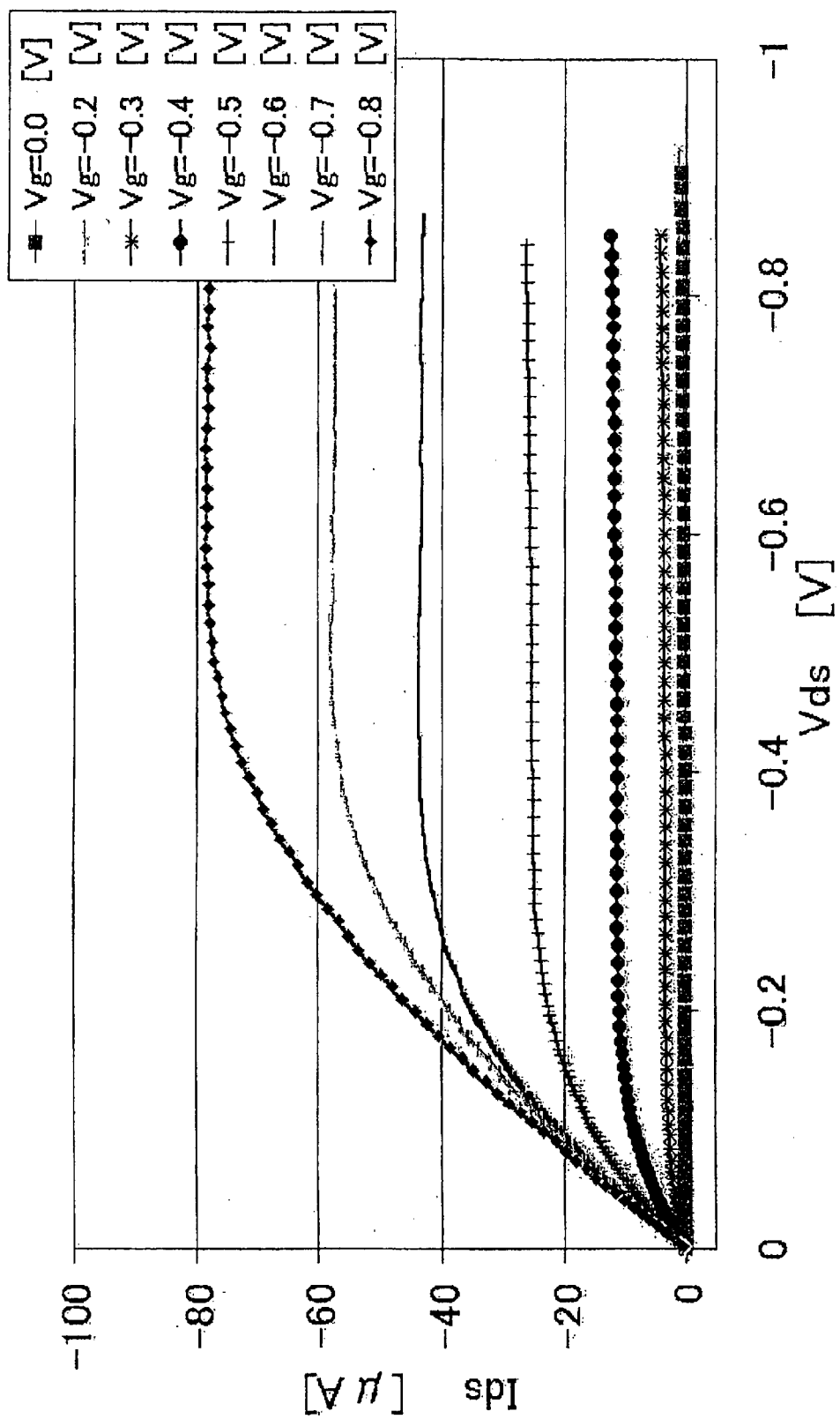
FIG. 6 is a graph showing static characteristics of the liquid-electrolyte-gate diamond FET fabricated by the second embodiment of the present invention (KOH aqueous solution; pH: 9)
Figure 7:
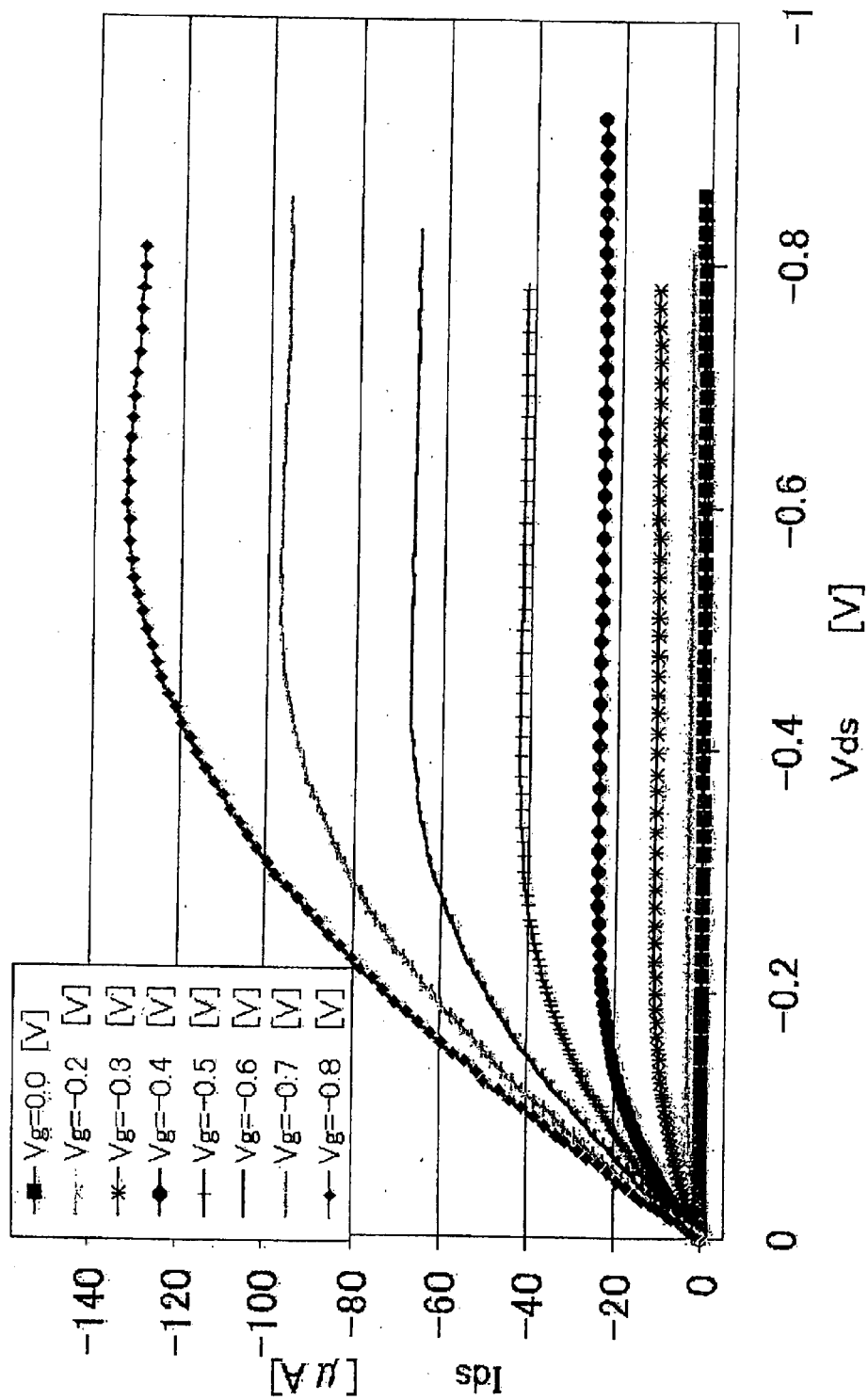
FIG. 7 is a graph showing static characteristics of the liquid-electrolyte-gate diamond FET fabricated by the second embodiment of the present invention (KOH aqueous solution; pH: 8)

FIGS. 5 to 7 are graphs showing static characteristics of a liquid-electrolyte-gate diamond FET fabricated according to the second embodiment of the present invention.

As described above, the exposed gate portion was filled with an alkali aqueous solution (KOH aqueous solution); and the diamond FET was operated to obtain the static characteristics shown in FIGS. 5 to 7.

FIG. 5 is a graph showing measurement results for the case where a pH 11 KOH aqueous solution is used; FIG. 6 is a graph showing measurement results for the case where a pH 9 KOH aqueous solution is used; and FIG. 7 is a graph showing measurement results for the case where a pH 8 KOH aqueous solution is used.

From these graphs as well, it can be confirmed that the drain current is controlled by means of a gate bias, which shows that the FET actually operates. This FET operates in a normally-off mode. In a region where the absolute value of the gate bias is small, the drain current is infinitesimal, and the absolute value of the drain current is seen to increase with a decrease in the absolute value of the gate bias. Within such a region, the FET is considered to be in an off mode. Static characteristics involving pinch off can be observed.

When the gate bias and the source-drain voltage were varied within the electric potential window, the FET was pinched off completely; i.e., the FET exhibited static characteristics such that saturation clearly occurred. Further, the FET was confirmed to have a constant threshold voltage of about –0.2V for the case where a pH 8 KOH was used, and was confirmed to be of a normally off type.

Next, measurement of the threshold voltage of the liquid-electrolyte-gate diamond FET of the present invention and its dependency on pH of liquid electrolyte will be described.

Figure 8:
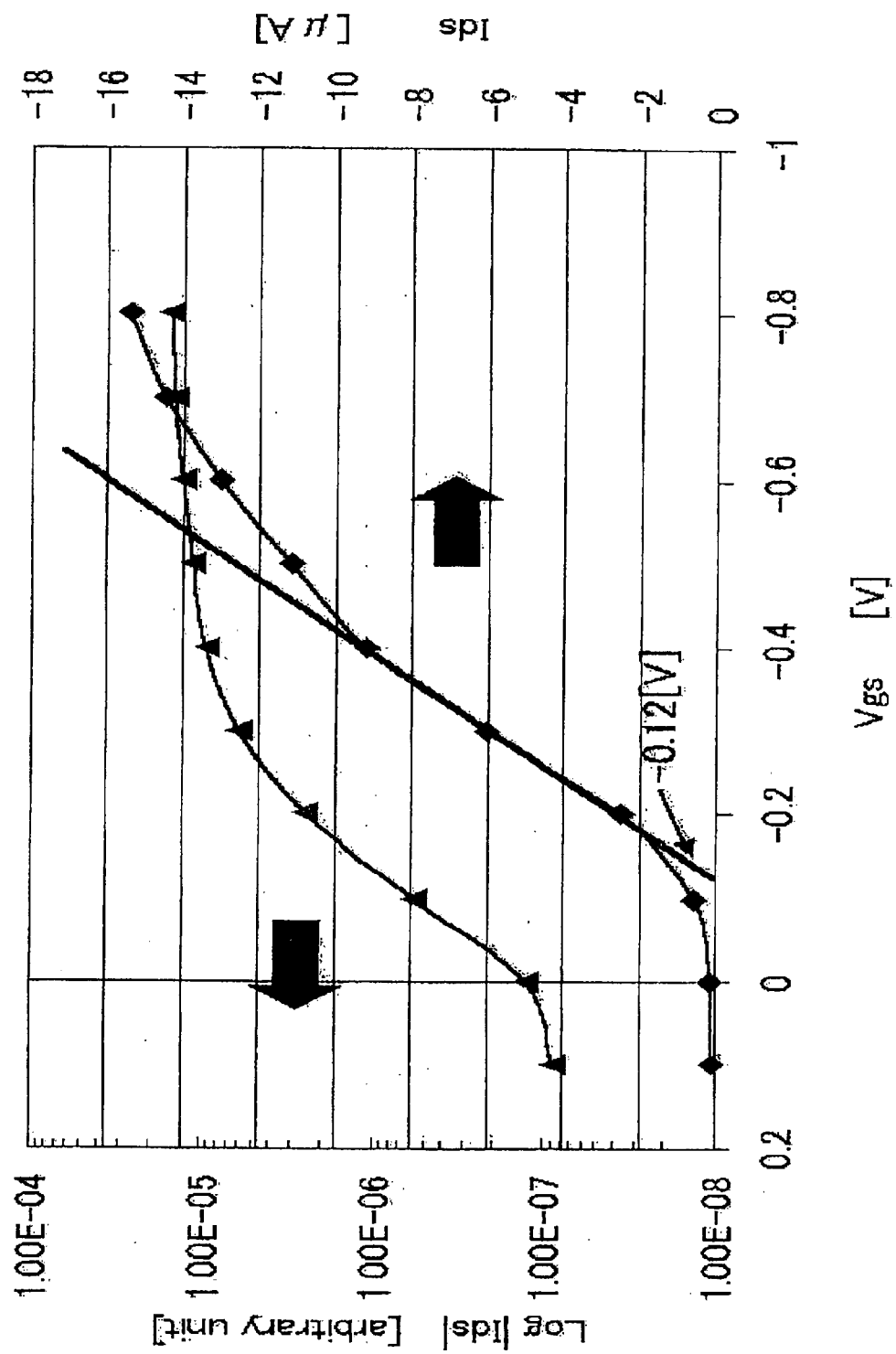
FIG. 8 is a graph showing the Vg-Ids characteristics of the liquid-electrolyte-gate diamond FET according to the present invention for the case of use of pH 11 KOH aqueous solution, along with its logarithmic representation.
Figure 9:
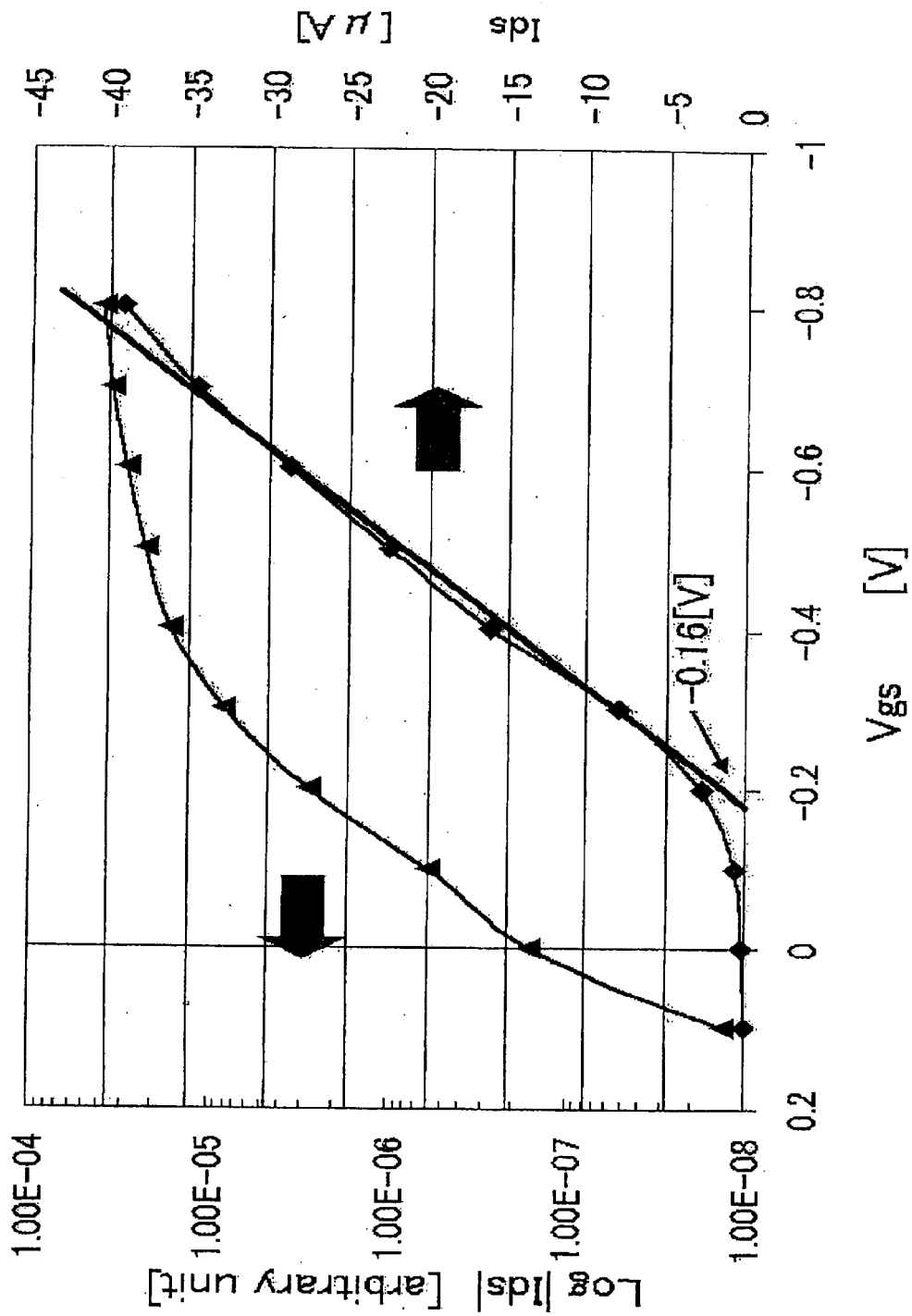
FIG. 9 is a graph showing the Vg-Ids characteristics of the liquid-electrolyte-gate diamond FET according to the present invention for the case of use of pH 8 KOH aqueous solution, along with its logarithmic representation.
Figure 10:
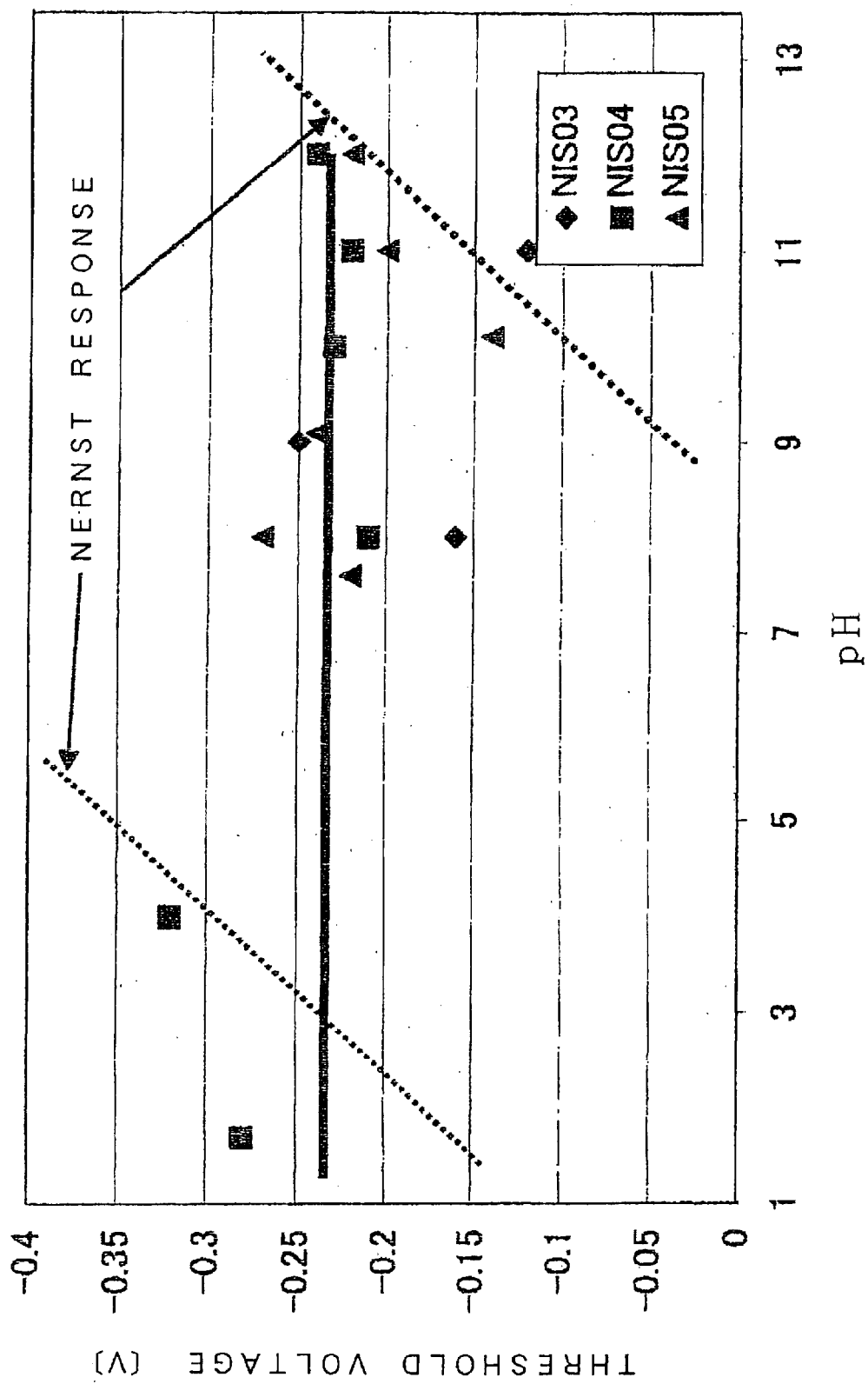
FIG. 10 is a graph showing the relationship between threshold voltage and pH measured for respective samples of the liquid-electrolyte-gate diamond FET according to the present invention.

FIG. 8 is a graph showing the Vg-Ids characteristics of the FET for the case where a pH 11 KOH aqueous solution is used, along with its logarithmic representation. FIG. 9 is a graph showing the Vg-Ids characteristics for the case where a pH 8 KOH aqueous solution is used, along with its logarithmic representation. In FIG. 8, the threshold voltage of the FET is –0.12V, and in FIG. 9, the threshold voltage of the FET is –0.16V. These threshold voltages are minus indicating a normally off type p-channel FET. Further, the same measurement was performed on various samples and at various pH values; and the threshold voltages of the samples were calculated. Thus, the characteristics as shown in FIG. 10 were obtained. FIG. 10 shows the relation between threshold voltage and pH in the samples (NIS03, NIS04, NIS05).

From the Log|Ids|-Vgs characteristics shown in FIG. 8, the ratio of on-state current to off-state current of the FET was found to be slightly less than 10,000. Considering that the employed polycrystalline diamond had an uneven surface, which had not been flattened after growth, this current ratio is very high.

Furthermore, it is shown that a polycrystalline diamond FET having a high current ratio can be used as an FET of low power consumption.

Further, since a hydrogen-terminated diamond surface is chemically stable, use of the hydrogen-terminated diamond as an electrochemical electrode having a wide electric potential window to be built in a secondary battery or biosensor has attracted a great deal of attention.

The present invention is expected to provide a biosensor in which the FET operates stably within a liquid electrolyte, such that a higher sensitivity can be realized by surface modification of an ion selective functional group on a channel which has no pH dependency.

In the embodiments, a KOH aqueous solution is used as a liquid electrolyte. However, the liquid electrolyte is not limited thereto. FET characteristics were observed for the case where other standard solutions were used, such as oxalate salt (pH 1.68), phthalate salt (pH 4), neutral phosphate salt (pH 7), borate salt (pH 9.18), and carbonate salt (pH 10.01).

In above-described embodiments, although a liquid vessel (insulator) is provided for each FET device, provision of a liquid vessel for each FET device is not necessarily required. A liquid electrolyte may be placed to fill the gate portions of several devices obtained at the fabrication step (d) of FIG. 3 or 4, and a common gate electrode may be disposed at an appropriate position.

The present invention is not limited to the embodiments described above. Numerous modifications and variations of the present invention are possible in light of the spirit of the present invention, and they are not excluded from the scope of the present invention.

As described above in detail, the present invention provides the following effects.

(A) There can be obtained a liquid-electrolyte-gate diamond FET which uses a liquid electrolyte as a gate, operates stably in the liquid electrolyte, and has a higher sensitivity realized through surface modification of an ion selective functional group on a channel which has no pH dependency.

(B) Since the threshold voltage has almost no pH dependency, the diamond FET can be used in an ion-sensitive FET measurement circuit as a reference FET for determining a reference potential.

INDUSTRIAL APPLICABILITY

The field effect transistor according to the present invention can effect selective detection of ions, and therefore can be applied to clinical testing, industrial measurement, and environmental measurement, with possible future application to a body-embedable sensor.

What is claimed is:

1. A field effect transistor comprising:
   (a) a diamond substrate;
   (b) a channel formed by a portion of a hydrogen-terminated surface on the diamond substrate comprising a hydrogen-terminated, undoped diamond layer, the portion being exposed to the outside between a source electrode and a drain electrode, the channel being formed on the diamond substrate;
   (c) a protective film coating top and side surfaces of the source electrode and the drain electrode; and
   (d) a gate formed of a liquid electrolyte in contact with the exposed portion, excluding the portion coated by the protective film, of the hydrogen-terminated surface of the diamond substrate.

2. A field effect transistor according to claim 1, characterized in that the diamond substrate is a monocrystalline or polycrystalline diamond thin film.

3. A field effect transistor according to claim 1, characterized in that the channel is a p channel.

4. A field effect transistor according to claim 3, characterized in that drain current is controlled by gate voltage, wherein the p channel can be pinched off when the gate voltage is 0 V.

5. A field effect transistor according to claim 3, characterized in that the p channel is of a normally off type.

6. A field effect transistor according to claim 1, characterized in that the hydrogen-terminated surface of the diamond substrate has a wide potential window, and the field effect transistor operates accurately within the range of the potential window.

7. A field effect transistor according to claim 1, characterized in that the liquid electrolyte is an alkaline solution.

8. A field effect transistor according to claim 7, characterized in that the liquid electrolyte is a KOH aqueous solution.

9. A field effect transistor according to claim 1, characterized in that the liquid electrolyte is an acidic solution.

10. A field effect transistor according to claim 1, characterized by having a threshold voltage which exhibits low dependence on the pH of the liquid electrolyte.

11. A field effect transistor according to claim 1, characterized by having a threshold voltage which is not affected by the environment.

* * * * *